United States Patent
Fang et al.

(10) Patent No.: US 11,584,729 B2
(45) Date of Patent: Feb. 21, 2023

(54) HYDROPHOBIC PALLADIUM/METAL ORGANIC FRAMEWORK MATERIAL, PREPARATION METHOD THEREOF, AND APPLICATION THEREFOR FOR USE IN SYNTHESIZING 2,5-DIMETHYLFURAN

(71) Applicant: NANJING AGRICULTURAL UNIVERSITY, Jiangsu (CN)

(72) Inventors: Zhen Fang, Jiangsu (CN); Hu Li, Jiangsu (CN)

(73) Assignee: NANJING AGRICULTURAL UNIVERSITY, Jiangsu (CN)

( * ) Notice: Subject to any disclaimer, the term of this patent is extended or adjusted under 35 U.S.C. 154(b) by 557 days.

(21) Appl. No.: 16/499,364

(22) PCT Filed: Oct. 18, 2017

(86) PCT No.: PCT/CN2017/106729
§ 371 (c)(1),
(2) Date: Sep. 30, 2019

(87) PCT Pub. No.: WO2018/176803
PCT Pub. Date: Oct. 4, 2018

(65) Prior Publication Data
US 2021/0101876 A1 Apr. 8, 2021

(30) Foreign Application Priority Data
Apr. 1, 2017 (CN) .......................... 201710211612.9

(51) Int. Cl.
*C07D 307/36* (2006.01)
*B01J 2/30* (2006.01)
(Continued)

(52) U.S. Cl.
CPC .............. *C07D 307/36* (2013.01); *B01J 2/30* (2013.01); *B01J 20/22* (2013.01); *B01J 20/3212* (2013.01); *B01J 23/44* (2013.01); *B01J 31/1691* (2013.01)

(58) Field of Classification Search
None
See application file for complete search history.

(56) References Cited

U.S. PATENT DOCUMENTS

2011/0263880 A1 10/2011 Rauchfuss et al.

FOREIGN PATENT DOCUMENTS

| CN | 103347885 A | 10/2013 | |
|---|---|---|---|
| JP | 2015027966 A | 2/2015 | |
| KR | 101846783 B1 * | 4/2018 | .............. B01J 27/04 |

OTHER PUBLICATIONS

Huang et al., "Polydimethylsiloxane Coating fora Palladium/MOF Composite: Highly Improved Catalytic Performance by Surface Hydrophobization." Angew. Chem. Int. Ed. (2016), 55, 7379-7383 (published online on May 4, 2016).*

(Continued)

*Primary Examiner* — Daniel Berns
(74) *Attorney, Agent, or Firm* — Gary J. Gershik

(57) ABSTRACT

A hydrophobic palladium/metal organic framework (MOF) material, which is a solid catalyst material obtained by taking a porous MOF as a carrier, introducing elementary palladium by means of an immersion-reduction method, and performing polydimethylsiloxane coating layer processing. A method which uses hydrophobic palladium/MOF material to selectively catalyze hexoses to prepare 2,5-dimethylfuran comprises: dissolving a hexose into an alcohol; using the hydrophobic palladium/MOF material as a catalyst and polymethylhydrosiloxane as a hydrogen donor, reacting at 70 to 130° C. for 0.25 to 12 h under the action of an acidic additive; the concentration of the hexose in the alcohol is 0.2

(Continued)

to 10 wt %, and the total amount of Pd contained in the hydrophobic palladium/MOF material relative to a hexose is 0.1 to 5 mol %. The hydrophobic palladium/MOF material has a stable structure, and under the same conditions, has a catalyzing efficiency which is significantly higher than that of commercially available palladium on carbon and common palladium/MOF materials.

14 Claims, 2 Drawing Sheets

(51) Int. Cl.
  *B01J 20/22*   (2006.01)
  *B01J 20/30*   (2006.01)
  *B01J 20/32*   (2006.01)
  *B01J 23/44*   (2006.01)
  *B01J 31/16*   (2006.01)

(56) References Cited

OTHER PUBLICATIONS

De S. et al., "One-Pot Conversions of Lignocellulosic and Algal Biomass into Liquid Fuels", ChemSusChem, 2012, pp. 1-9.
Hu L. et al., "Highly Selective Hydrogenation of Biomass-Derived 5-Hydroxymethylfurfural into 2,5-bis (hydroxymethyl) furan over an Acid-Base Bifunctional Hafnium-Based Coordination Polymer Catalyst", The Royal Society of Chemistry, 2013, pp. 1-10.
Li H. et al., "Hydrophobic Pd Nanocatalysts for One-pot and High-yield Production of Liquid 1-10 Furanic Biofuels at Low Temperatures", Applied Catalysis B: Environmental, vol. 215, Jun. 18, 2017, pp. 19-23.
Román-Leshkov Y. et al., "Production of Dimethylfuran for Liquid Fuels from Biomass-derived Carbohydrates", Nature, vol. 447, Jun. 21, 2007, pp. 982-986.
Volkov A. et al., "Mild Deoxygenation of Aromatic Ketones and Aldehydes over Pd/C Using Polymethylhydrosiloxane as the Reducing Agent", Angew. Chem. Int. Ed., 2015, vol. 54, pp. 1-6.
Zhou P. and Zhang Z., "One-pot catalytic conversion of carbohydrates into furfural and 5-hydroxymethylfurfural", The Royal Society of Chemistry, 2016, pp. 1-19.
Zu Y. et al., "Efficient production of the liquid fuel 2,5-dimethylfuran from 5-hydroxymethylfurfural over Ru/Co3O4 catalyst", Applied Catalysis B, Environmental, 2013, pp. 1-21.
International Search Report dated Jan. 24, 2018 in connection with PCT International Application No. PCT/CN2017/106729.
Written Opinion (form PCT/ISA/237) dated Jan. 24, 2018 in connection with PCT International Application No. PCT/CN2017/106729.

\* cited by examiner

HYDROPHOBIC PALLADIUM/METAL ORGANIC FRAMEWORK MATERIAL, PREPARATION METHOD THEREOF, AND APPLICATION THEREFOR FOR USE IN SYNTHESIZING 2,5-DIMETHYLFURAN

CROSS-REFERENCE TO RELATED APPLICATIONS

This application is a § 371 national stage of PCT International Application No. PCT/CN2017/106729, filed Oct. 18, 2017, claiming priority of Chinese Patent Application No. 201710211612.9, filed Apr. 1, 2017, the contents of each of which are hereby incorporated by reference into the application.

BACKGROUND

Technical Field

The present invention relates to a hydrophobic palladium/metal organic framework (MOF) material, a preparation method thereof, and application thereof, and more particularly relates to a palladium/MOF material with uniform active site distribution, stable structure and high hydrophobicity and a preparation method thereof, and application of the material in catalysis of hexoses to prepare 2,5-dimethylfuran.

Related Art

In recent years, 2,5-dimethylfuran has been reported to be a liquid biofuel with great application prospect, and the energy density (31.5 MJ/L), octane number (119) and boiling point (92 to 94° C.) are all equivalent to or even greater than those of gasoline (the energy density is 35 MJ/L, the octane number is 95.8 and the boiling point is 96.3° C.)[1]. Usually, under the action of a metal catalyst (such as Pd, Pt, Ru, Ni and Cu), 5-hydroxymethylfurfural can be converted to 2,5-dimethylfuran by hydrogenated dehydration reaction[2]. However, conditions such as reaction temperature, time and hydrogen pressure are relatively severe, and the yield of the obtained 2,5-dimethylfuran is often unsatisfactory.

Lignocellulose and its derivatives thereof are currently known renewable organic carbon sources in the largest storage amount, and the carbohydrate component content may be up to 75%. It is worth noting that 5-hydroxymethylfurfural is a dehydration product of hexa-monosaccharide, which may be obtained efficiently under acid catalysis[3]. Therefore, direct use of a hexose as a substrate to prepare 2,5-dimethylfuran is more in line with the sustainable production concept, and may also greatly reduce the production cost and reduce the pressure on shortage of raw materials required for preparing biodiesel. Based on the above considerations, Dumesic research group firstly reports a method for preparing 2,5-dimethylfuran by catalyzing fructose by a two-step method (a fluid bed), comprising: (1) catalyzing, by HCl, fructose to be dehydrated to obtain 5-hydroxymethylfurfural; (2) catalyzing, by CuRu/C, a separated and purified intermediate to undergo hydrogenolysis reaction. The total yield of the obtained 2,5-dimethylfuran in the two steps is about 60%[4]. Similarly, metals Pd and Ru supported by acidic media or carriers also have recently been reported to catalyze fructose or glucose to be converted to 2,5-dimethylfuran via two or more steps of reaction processes, but the yield is often less than 60%[5-7]. Therefore, searching for a 2,5-dimethylfuran preparation method with high efficiency and simple process is a prerequisite for achieving large-scale or industrial production of the 2,5-dimethylfuran.

Similar to alcohol and formic acid etc., polymethylhydrosiloxane is stable to water and air, inexpensive and low in toxicity, and is widely used as a liquid donor to catalyze the reduction of compounds such as amides, esters, hydroxyl groups, nitro groups and carbonyl groups[8]. Metal ions or elemental metals acting on the polymethylhydrosiloxane show relatively high selectivity to target products, but there are deficiencies such as low substrate conversion rate and long reaction time. It is speculated that this has a close relation with the phenomena including that polymethylhydrosiloxane serving as a polymer with relatively high hydrophobicity may hardly directly act on catalysis sites and substrates during the reaction. Therefore, it is particularly necessary to regulate the surface hydrophilicity and hydrophobicity of a catalyst material. Meanwhile, catalytic conversion of hexoses (especially hexa-polysaccharose) to 2,5-dimethylfuran often involves many reaction steps such as hydrolysis, dehydration and hydrogenation. Correspondingly, how to effectively construct active sites such as acid and metal of the catalyst material and select suitable hydrogen donors is the key to efficient preparation of 2,5-dimethylfuran.

REFS

[1] Hu, L.; Lin, L.; Liu, S. "Chemoselective hydrogenation of biomass-derived 5-hydroxymethylfurfural into the liquid biofuel 2,5-dimethylfuran." Industrial & Engineering Chemistry Research, 2014, 53, 9969-9978.
[2] Saha, B.; Abu-Omar, M. M. "Current technologies, economics, and perspectives for 2,5-dimethylfuran production from biomass-derived intermediates." ChemSusChem, 2015, 8, 1133-1142.
[3] Zhou, P.; Zhang, Z. "One-pot catalytic conversion of carbohydrates into furfural and 5-hydroxymethylfurfural." Catalysis Science & Technology, 2016, 6, 3694-3712.
[4] Roman-Leshkov, Y.; Barrett, C. J.; Liu, Z. Y.; Dumesic, J. A. "Production of dimethylfuran for liquid fuels from biomass-derived carbohydrates." Nature, 2007, 447, 982-985.
[5] Zu, Y.; Yang, P.; Wang, J.; Liu, X.; Ren, J.; Lu, G.; Wang, Y. "Efficient production of the liquid fuel 2,5-dimethylfuran from 5-hydroxymethylfurfural over RU/$Co_3O_4$ catalyst." Applied Catalysis B: Environmental, 2014, 146, 244-248.
[6] Gallo, J. M. R.; Alonso, D. M.; Mellmer, M. A.; Dumesic, J. A. "Production and upgrading of 5-hydroxymethylfurfural using heterogeneous catalysts and biomass-derived solvents." Green Chemistry, 2013, 15, 85-90.
[7] De, S.; Dutta, S.; Saha, B. "One-pot conversions of lignocellulosic and algal biomass into liquid fuels." ChemSusChem, 2012, 5, 1826-1833.
[8] Volkov, A.; Gustafson, K. P.; Tai, C. W.; Verho, O.; Bäckvall, J. E.; Adolfsson, H. "Mild deoxygenation of aromatic ketones and aldehydes over Pd/C using polymethylhydrosiloxane as the reducing agent." Angewandte Chemie International Edition, 2015, 54, 5122-5126.

SUMMARY

The objective of the present invention is to overcome the existing shortcomings of high cost of preparation of 2,5-dimethylfuran, complex process and severe reaction conditions. A catalyst material with high hydrophobicity and uniform active site distribution is synthesized by selecting polymethylhydrosiloxane as a hydrogen donor and selecting alcohol as a solvent, and performing polydimethylsiloxane coating layer processing on a Pd/MOF. The catalyst material shows high activity and stability in the reaction of catalyzing hexoses to prepare 2,5-dimethylfuran, and is good in reusability.

The objective of the present invention is achieved by the following technical solution:

A hydrophobic palladium/MOF material, which is obtained by selecting an MOF as a carrier, dispersing Pd salt into pores of the MOF through immersion treatment to prepare a palladium/MOF material, reducing the palladium/MOF material in a hydrogen atmosphere at 200 to 300° C. for 2 to 5 h, and finally performing polydimethylsiloxane coating layer processing.

The MOF is obtained by dissolving transition metal salt and an equivalent mole number of terephthalic acid in deionized water or N,N-dimethylformamide, performing hydrothermal treatment at 120 to 220° C. for 12 to 72 h, and then performing washing and vacuum drying. The transition metal salt is chloride salt or nitrate of $Cu^{2+}$, $Al^{3+}$, $Cr^{3+}$, $Fe^{3+}$ or $Zr^{4+}$. The mole ratio of the transition metal salt to the deionized water or the N,N-dimethylformamide is 1:(100 to 300). Precipitations are easily separated out by the hydrothermal treatment within the concentration range, and precipitations are hardly separated out beyond the concentration range. The washing is performed with the deionized water or ethanol. The temperature of the vacuum drying is 90 to 100° C.

The immersion treatment is: dissolving the Pd salt in water or alcohol, adding the MOF, performing ultrasonic treatment for 15 to 60 min, stirring at room temperature for 12 to 24 h, and then centrifuging, washing, drying and grinding the mixture to obtain the palladium/MOF material. Metered by Pd, the usage amount of the Pd salt is 1 to 20 wt % of the MOF, preferably 1 to 6 wt %. The Pd salt is palladium chloride, palladium nitrate, palladium acetate and palladium sulfate, and the alcohol is methanol, ethanol, n-butanol and n-hexanol. The centrifugal rotational speed is 6000 to 8000 r/min. The mixture is washed with the N,N-dimethylformamide for 3 times, and the volume/mass ratio of N,N-dimethylformamide to the MOF is (4 to 6) mL: 1 g per wash. The drying method is vacuum drying at 80 to 100° C. for 4 to 8 h.

The reduction treatment is: flatly laying solid powder of the palladium/MOF material into a porcelain crucible in a sealed tubular furnace, feeding 20% $H_2$/Ar at a flow rate of 30 $cm^3$/min, performing programmed heating according to a heating rate of 10° C./min to 200-300° C., and maintaining the temperature for 2 to 5 h.

The polydimethylsiloxane coating layer processing is: flatly laying the reduced palladium/MOF material into a watch glass, placing the watch glass into an inner container of a hydrothermal reactor with polydimethylsiloxane, sealing the hydrothermal reactor, transferring the hydrothermal reactor into an oven at 190 to 220° C., performing thermal treatment for 15 to 45 min, applying the polydimethylsiloxane to the surface of the palladium/MOF material by evaporation, and taking out the reactor for natural cooling to room temperature. The polydimethylsiloxane is excessive, and preferably, the mass ratio of the polydimethylsiloxane to the reduced palladium/MOF material is 1:1.

The present invention further provides a preparation method of a hydrophobic palladium/MOF material, comprising the following steps:

(1) dissolving Pd salt in water or alcohol, adding an MOF serving as a carrier, performing ultrasonic treatment for 15 to 60 min, stirring at room temperature for 12 to 24 h, and then centrifuging, washing, drying and grinding the mixture to obtain a palladium/MOF material, wherein metered by Pd, the usage amount of the Pd salt is 1 to 20 wt % of the mass of the MOF, preferably 1 to 6 wt %, and the Pd salt is palladium chloride, palladium nitrate, palladium acetate and palladium sulfate, and the alcohol is methanol, ethanol, n-butanol and n-hexanol; and (2) reducing the palladium/MOF material in a hydrogen atmosphere at 200 to 300° C. for 2 to 5 h, and performing polydimethylsiloxane coating layer processing on the reduced palladium/MOF material to obtain the palladium/MOF material with high hydrophobicity and uniform active site distribution.

In the step (1), the mass-to-volume ratio of the MOF to the water or alcohol is 1 g:(4.5 to 6) mL.

The present invention also relates to application of the hydrophobic palladium/MOF material in catalyzing hexoses to prepare 2,5-dimethylfuran.

A method for using the hydrophobic palladium/MOF material of the present invention to selectively catalyze hexoses to prepare 2,5-dimethylfuran comprises the following steps: dissolving a hexose in alcohol for reaction at 70 to 130° C. for 0.25 to 12 h under the action of an acidic additive by taking the hydrophobic palladium/MOF material as a catalyst and taking polymethylhydrosiloxane as a hydrogen donor; and at the end of the reaction, separating the catalyst from a product via centrifugation, wherein the concentration of the hexose in the alcohol is 0.2 to 10 wt %; metered by Pd, the usage amount of the hydrophobic palladium/MOF material is 0.1-5 mol % of the usage amount of the hexose; and the usage amount of the polymethylhydrosiloxane is 5 to 10 mol % of the usage amount of the hexose, preferably 6 to 10 mol %.

Preferably, the concentration of the hexose in the alcohol is 0.5 to 5 wt %; and metered by Pd, the usage amount of the hydrophobic palladium/MOF material is 0.5 to 3 mol % of the usage amount of the hexose. More preferably, the concentration of the hexose in the alcohol is 1 to 5 wt %; and metered by Pd, the usage amount of the hydrophobic palladium/MOF material is 0.5 to 3 mol % of the usage amount of the hexose.

Preferably, the reaction temperature is 100 to 120° C., and the reaction time is 2 to 8 h.

The hexose is fructose, mannose, glucose, or disaccharide, such as saccharose and cellobiose, formed by dehydration condensation of the above monosaccharide, or polysaccharide, such as inulin, formed by dehydration condensation of the above monosaccharide. The alcohol is methanol, ethanol, n-propanol, isopropanol, n-butanol, isobutanol and n-hexanol.

The acidic additive is hydrochloric acid, sulfuric acid or chlorobenzene. The usage amount of the acidic additive is 3 to 9 mol %, preferably 6 mol %, of the usage amount of the hexose. The function of the acidic additive is to catalyze the hexose to be dehydrated to prepare a 5-hydroxymethylfurfural intermediate.

A preferred solution of the method for selectively catalyzing the hexose to prepare the 2,5-dimethylfuran also comprises: regenerating the catalyst material: centrifuging out the catalyst material from the reaction liquid, washing the catalyst material with water and ethanol each for 3 to 5 times, performing vacuum drying at 100° C. for 10 h, and grinding the material to obtain a regenerated catalyst material.

Compared with commercially available Pd/C and common palladium/MOF catalyst materials, the hydrophobic palladium/MOF material prepared by the method of the present invention has the advantage that under the same conditions, the yield of the 2,5-dimethylfuran prepared by catalyzing the hexose is increased by about 45% and 25% respectively.

Compared with the prior art, the present invention has the beneficial effects that:

(1) The catalyst material of the present invention is high in hydrophobicity, uniform in active site distribution, easy to separate, recycle and reuse and good in reusability, and the preparation method is simple;

(2) The hydrophobic palladium/MOF material of the present invention has wide applicability to catalyzing different hexoses to prepare the 2,5-dimethylfuran, and has mild reaction conditions and high activity.

DETAILED DESCRIPTION

The technical solutions of the present invention are further described below in detail in combination with the embodiments, but are not intended to limit the present invention.

Embodiment 1

(1) Preparation of a Common Pd/MIL-53(Al) Catalyst Material

Materials were fed according to a mole ratio of $Al(NO_3)_3 \cdot 9H_2O$:terephthalic acid:water of 1:1:100, and were mixed and added into a 25 mL hydrothermal reactor, and the mixture was subjected to standing hydrothermal treatment in an oven at 220° C. for 72 h, then was washed with deionized water and was vacuum-dried at 100° C. to obtain an MIL-53(Al) carrier.

0.25 g of the prepared MIL-53(Al) carrier was added into a methanol (1.2 mL) solution with 13 mg of $PdCl_2$ dissolved; ultrasonic treatment was performed for 3.0 min, and room-temperature stirring was performed for 24 h; then the solution was centrifuged at 8000 r/min, washed with N,N-dimethylformamide for 3 times, 10 mL per wash, vacuum-dried at 90° C. for 6 h and ground; and finally, reduction was performed in a hydrogen atmosphere at 250° C. for 3 h (the flow rate of 20% of $H_2$/Ar was 30 cm$^3$/min, and the heating rate was 10° C./min) to obtain the common Pd/MIL-53(Al) catalyst material.

Figure 1:
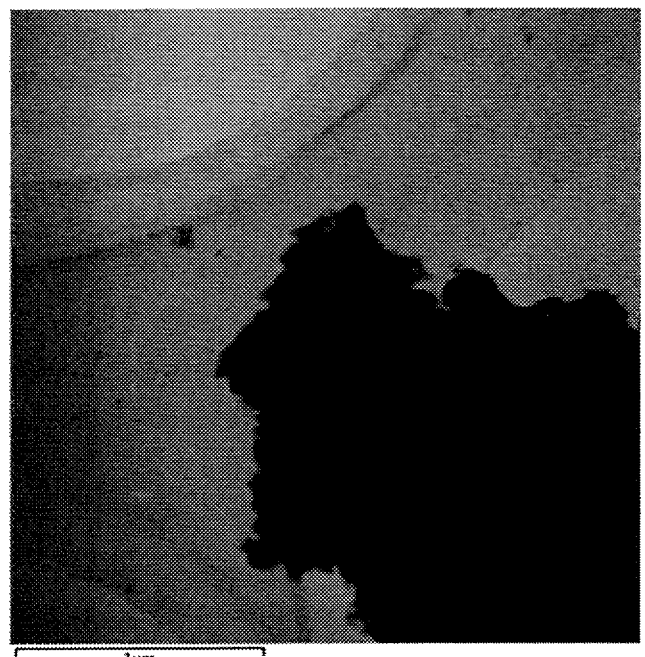
FIG. 1 is a High-Angle Annular Dark Field-Scanning Transmission Electron Microscope (HAADF-STEM) of Pd/MIL-53(Al).
Figure 2:
FIG. 2 is an X-ray Energy-Dispersion Spectroscopy (EDS) distribution image of the element Al in Pd/MIL-53 (Al).
Figure 3:
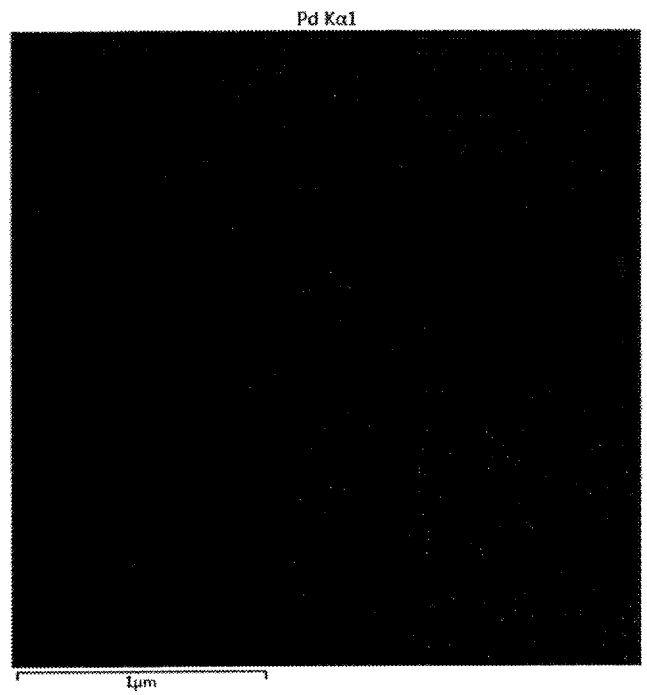
FIG. 3 is an X-ray Energy-Dispersion Spectroscopy (EDS) distribution image of the element Pd in Pd/MIL-53 (Al).
Figure 4:
FIG. 4 is a surface water contact angle (CA: 24 degrees) of common Pd/MIL-53(Al).

It can be seen from the High-Angle Annular Dark Field-Scanning Transmission Electron Microscope (HAADF-STEM) in FIG. 1 and the X-ray Energy-Dispersion Spectroscopy (EDS) distribution images of the elements Al and Pd in FIGS. 2 and 3 that the Pd/MIL-53(Al) catalyst materials obtained by immersion reduction had uniformly dispersed Al and Pd active sites. Moreover, the surface water contact angle of the Pd/MIL-53(Al) was only 24 degrees (FIG. 4), indicating that the common Pd/MIL-53(Al) had relatively good hydrophilicity.

(2) Preparation of a Hydrophobic Pd/MIL-53(Al) Catalyst Material

Solid powder of the common Pd/MIL-53(Al) (20 mg) was weighed and then was uniformly flatly laid in a micro watch glass; the watch glass was placed into an inner container of a hydrothermal reactor with an equal amount of polydimethylsiloxane; the reactor was transferred into an oven at 205° C. after being sealed, and underwent thermal treatment for 30 min; and then the reactor was taken out for natural cooling to room temperature to obtain the hydrophobic Pd/MIL-53(Al) catalyst material (the Pd content was 2.8 wt %).

Figure 5:
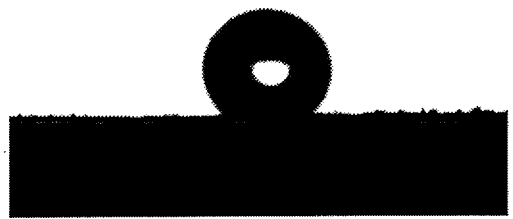
FIG. 5 is a surface water contact angle (CA: 135 degrees) of hydrophobic Pd/MIL-53 (Al).

It can be seen from FIG. 5 that the surface water contact angle of the hydrophobic Pd/MIL-53(Al) catalyst material was 135 degrees, indicating that a modified material obtained by performing polydimethylsiloxane coating layer processing on the Pd/MIL-53(Al) had good hydrophobicity.

(3) Preparation of 2,5-Dimethylfuran by Catalyzing Fructose n-Butanol (2 mL) was added into a pressure-resistant glass reaction tube (volume: 15 mL); fructose was dissolved in n-butanol to prepare a mixed solution at 5 wt %; then the hydrophobic Pd/MIL-53(Al) catalyst material (the total amount of Pd was 1 mol % of fructose) was added, and a small amount of chlorobenzene (6 mol % of the usage amount of fructose) and polymethylhydrosiloxane (10 mol % of the usage amount of fructose) were added dropwise; the pressure-resistant glass reaction tube was placed in an oil bath pot at 110° C. and was heated and stirred for 2.5 h; at the end of the reaction, a solid catalyst was separated by centrifugation and filtration; the conversion rate of fructose in the reaction liquid was measured by high performance liquid chromatography, and the yield of the 2,5-dimethylfuran was measured by gas chromatography. The conversion rate of fructose was 100%, and the yield of the 2,5-dimethylfuran was 93%.

(4) Regeneration of the Hydrophobic Pd/MIL-53(Al) Catalyst Material

The solid catalyst was washed with water and ethanol each for 4 times, and then was dried at 100° C. for 10 h and ground to obtain a regenerated catalyst.

The regenerated catalyst was used to catalyze fructose to prepare 2,5-dimethylfuran, and the usage amounts of the various raw materials and the reaction conditions were the same as those in Embodiment 1(3). It was detected that the conversion rate of fructose was 99%, and the yield of 2,5-dimethylfuran was 91%. Moreover, after the catalyst was repeatedly used by the same method for 5 times, the yield of the obtained 2,5-dimethylfuran was 87%, indicating that the hydrophobic Pd/MIL-53(Al) catalyst material had good reusability.

Comparison Example 1

Two mL of n-butanol was added into a pressure-resistant glass reaction tube (volume: 15 mL); fructose was dissolved in n-butanol to prepare a mixed solution at 5 wt %; then the common Pd/MIL-53(Al) catalyst material (the total amount of Pd is 1 mol % of fructose) obtained in Embodiment 1(1) was added, and a small amount of chlorobenzene (6 mol % of the usage amount of fructose) was added dropwise; the pressure-resistant glass reaction tube was placed in an oil bath pot at 110° C. and was heated and stirred for 2.5 h; at the end of the reaction, a solid catalyst was separated by filtration; the conversion rate of fructose in the reaction liquid was measured by high performance liquid chromatography, and the yield of the 2,5-dimethylfuran was measured by gas chromatography. The conversion rate of fructose was 100%, and the yield of the 2,5-dimethylfuran was 78%.

The separated solid catalyst was washed with water and ethanol each for 4 times, and then was dried at 100° C. for 10 h and ground to obtain a regenerated catalyst. The regenerated catalyst was used to catalyze the fructose to prepare 2,5-dimethylfuran, and the usage amounts of the various raw materials and the reaction conditions were the same as those in Embodiment 1(3). It was detected that the conversion rate of fructose in the reaction mixed solution was 90%, and the yield of the 2,5-dimethylfuran was 65%.

Comparison Example 2

Pd/C (5 wt %) (purchased from Beijing Innochem Technology Co., Ltd.) was used to catalyze fructose to prepare 2,5-dimethylfuran; the usage amounts of the various raw materials and the reaction conditions were the same as those in Embodiment 1(3). The conversion rate of fructose in the reaction liquid was measured by high performance liquid chromatography, and the yield of 2,5-dimethylfuran was measured by gas chromatography. The conversion rate of fructose was 85%, and the yield of 2,5-dimethylfuran was 48%.

The regeneration of Pd/C was the same as that in Embodiment 1(4). The regenerated Pd/C was used to catalyze fructose to prepare 2,5-dimethylfuran. The usage amounts of the various raw materials and the reaction conditions were the same as those in Embodiment 1(3). It was detected that the conversion rate of fructose was 76%, and the yield of 2,5-dimethylfuran was 25%.

Embodiment 2

(1) Preparation of a Hydrophobic Pd/MIL-101(Cr) Catalyst Material

Materials were fed according to a mole ratio of $Cr(NO_3)_3 \cdot 9H_2O$:terephthalic acid:water of 1:1:200, and were mixed and added into a 25 mL hydrothermal reactor, and the mixture was subjected to standing hydrothermal treatment in an oven at 220° C. for 12 h, then was washed with ethanol and was vacuum-dried at 90° C. to obtain an MIL-101(Cr) carrier.

0.25 g of the prepared MIL-101(Cr) carrier was added into a methanol (1.2 mL) solution with 21 mg of $PdCl_2$ dissolved; ultrasonic treatment was performed for 30 min, and room-temperature stirring was performed for 24 h; then the solution was centrifuged at 8000 r/min, washed with N,N-dimethylformamide for 3 times, 10 mL per wash, vacuum-dried at 90° C. for 6 h and ground; and finally, reduction was performed in a hydrogen atmosphere at 250° C. for 3 h (the flow rate of 20% of $H_2$/Ar was 30 cm$^3$/min, and the heating rate was 10° C./min) to obtain a common Pd/MIL-101(Cr) catalyst material.

20 mg of solid powder of the common Pd/MIL-101(Cr) was weighed and then was uniformly flatly laid in a micro watch glass; the watch glass was placed into an inner container of a hydrothermal reactor with an equal amount of polydimethylsiloxane; the reactor was transferred into an oven at 205° C. after being sealed, and underwent thermal treatment for 30 min; and then the reactor was taken out for natural cooling to room temperature to obtain the hydrophobic Pd/MIL-101(Cr) catalyst material (the Pd content was 4.8 wt %).

(2) Preparation of 2,5-Dimethylfuran by Catalyzing Saccharose 5 mL of ethanol was added into a pressure-resistant glass reaction tube (volume: 15 mL); saccharose was dissolved in ethanol to prepare a mixed solution at 5 wt %; then the hydrophobic Pd/MIL-101(Cr) catalyst material (the total amount of Pd was 2.5 mol % of saccharose) was added, and a small amount of hydrochloric acid (6 mol % of the usage amount of saccharose) and polymethylhydrosiloxane (10 mol % of the usage amount of saccharose) were added dropwise; the pressure-resistant glass reaction tube was placed in an oil bath pot at 120° C. and was heated and stirred for 4 h; at the end of the reaction, a solid catalyst was separated by filtration; the conversion rate of the saccharose in the reaction liquid was measured by high performance liquid chromatography, and the yield of 2,5-dimethylfuran was measured by gas chromatography. The conversion rate of saccharose was 100%, and the yield of 2,5-dimethylfuran was 75%.

Embodiment 3

(1) Preparation of Hydrophobic Pd/UiO-66(Zr) Catalyst Material

Materials were fed according to a mole ratio of $ZrCl_4$:terephthalic acid:N,N-dimethylformamide of 1:1:300, and were mixed and added into a 25 mL hydrothermal reactor, and the mixture was subjected to standing hydrothermal treatment in an oven at 130° C. for 24 h, then was washed with ethanol and was vacuum-dried at 90° C. to obtain a UiO-66(Zr) carrier.

0.25 g of the prepared UiO-66(Zr) carrier was added into a methanol (1.2 mL) solution with 6 mg of $PdCl_2$ dissolved; ultrasonic treatment was performed for 30 min, and room-temperature stirring was performed for 24 h; then the solution was centrifuged at 8000 r/min, washed with N,N-dimethylformamide for 3 times, 10 mL per each wash, vacuum-dried at 90° C. for 6 h and ground; and reduction was performed in a hydrogen atmosphere at 250° C. for 3 h (the flow rate of 20% of $H_2$/Ar was 30 cm$^3$/min, and the heating rate was 10° C./min) to obtain a common Pd/UiO-66(Zr) catalyst material.

20 mg of solid powder of the common Pd/UiO-66(Zr) was weighed and then was uniformly flatly laid in a micro watch glass; the watch glass was placed into an inner container of a hydrothermal reactor with an equal amount of polydimethylsiloxane; the reactor was transferred into an oven at 205° C. after being sealed, and underwent thermal treatment for 30 min; and then the reactor was taken out for natural cooling to room temperature to obtain the hydrophobic Pd/UiO-66(Zr) catalyst material (the Pd content was 1.1 wt %).

(2) Preparation of 2,5-Dimethylfuran by Catalyzing Glucose 3 mL of n-butanol was added into a pressure-resistant glass reaction tube (volume: 15 mL); glucose was dissolved in n-butanol to prepare a mixed solution at 1 wt %; then the hydrophobic Pd/UiO-66(Zr) catalyst material (the total amount of Pd was 0.5 mol % of glucose) was added, and a small amount of sulfuric acid (6 mol % of the usage amount of glucose) and polymethylhydrosiloxane (8 mol % of the usage amount of glucose) were added dropwise; the pressure-resistant glass reaction tube was placed in an oil bath pot at 100° C. and was heated and stirred for 6 h; at the end of the reaction, a solid catalyst was separated by filtration; the conversion rate of glucose in the reaction liquid was measured by high performance liquid chromatography, and the yield of the 2,5-dimethylfuran was measured by gas chromatography. The conversion rate of glucose was 97% and the yield of 2,5-dimethylfuran was 68%.

Embodiment 4

The hydrophobic Pd/MIL-53(Al) catalyst material of Embodiment 1 was used to catalyze inulin to prepare 2,5-dimethylfuran.

2 mL of methanol was added into a pressure-resistant glass reaction tube (volume: 15 mL); inulin was dissolved in methanol to prepare a mixed solution at 1.5 wt %; then the hydrophobic Pd/MIL-53(Al) catalyst material (the total amount of Pd was 1 mol % of inulin) was added, and a small amount of chlorobenzene (6 mol % of the usage amount of inulin) and polymethylhydrosiloxane (6 mol % of the usage amount of inulin) were added dropwise; the pressure-resistant glass reaction tube was placed in an oil bath pot at 120° C. and was heated and stirred for 8 h; at the end of the reaction, a solid catalyst was separated by filtration; the conversion rate of inulin in the reaction liquid was measured by high performance liquid chromatography, and the yield of 2,5-dimethylfuran was measured by gas chromatography. The conversion rate of inulin was 98%, and the yield of 2,5-dimethylfuran was 87%.

What is claimed is:

1. A process for preparing 2,5-dimethylfuran comprising contacting a hexose with a hydrophobic palladium/metal organic framework (MOF) material under conditions for catalyzing hexoses to prepare 2,5-dimethylfuran;
    wherein a MOF is obtained by dissolving a chloride salt or a nitrate salt of $Cu^{2+}$, $Al^{3+}$, $Cr^{3+}$, $Fe^{3+}$, or $Zr^{4+}$, and an equivalent mole number of terephthalic acid in deionized water or N,N-dimethylformamide, performing hydrothermal treatment at 120 to 220° C. for 12 to 72 h, and then performing filtering, washing and vacuum drying;
    wherein the hydrophobic palladium/MOF material is obtained by immersing the MOF serving as a carrier to obtain a palladium/MOF material, reducing the palladium/MOF material in a hydrogen atmosphere at 200 to 300° C. for 2 to 5 h, and finally performing polydimethylsiloxane coating layer processing;
    wherein immersing the MOF comprises dissolving the a Pd salt in water or alcohol, adding the MOF, performing ultrasonic treatment for 15 to 60 min, stirring at room temperature for 12 to 24 h, and then centrifuging, washing, drying and grinding the mixture to obtain the palladium/MOF material;
    wherein the amount of the Pd salt, based on the weight of Pd, is 1 to 20 wt % of the mass of the MOF; the Pd salt is palladium chloride, palladium nitrate, palladium acetate, or palladium sulfate; and the alcohol is methanol, ethanol, n-butanol, or n-hexanol.

2. The process according to claim 1, wherein the hexose is fructose, mannose, glucose, saccharose, cellobiose or inulin; and the alcohol is methanol, ethanol, n-propanol, isopropanol, n-butanol, isobutanol or n-hexanol.

3. The process according to claim 1, wherein the acidic additive is hydrochloric acid, sulfuric acid or chlorobenzene, and the amount of the acidic additive is 3 to 9 mol % of the amount of the hexose.

4. The process according to claim 1, further comprising regenerating the hydrophobic palladium/MOF material by centrifuging out the catalyst material from the reaction liquid, washing the catalyst material with water and ethanol each for 3 to 5 times, performing vacuum drying at 100° C. for 10 h, and grinding the material to obtain a regenerated catalyst material.

5. The process of claim 1, wherein the concentration of hexose in the alcohol is 0.5 to 5 wt %, and wherein the amount of the hydrophobic palladium/MOF material, based on the amount of Pd, is 0.5 to 3 mol %.

6. The process of claim 1, wherein immersing the MOF comprises dissolving 1 to 6 wt % Pd salt in water or alcohol, based on the weight of Pd.

7. The process according to claim 1, wherein the amount of Pd salt, based on the weight of Pd, is 1 to 6 wt % of the mass of the MOF.

8. A process for preparing 2,5-dimethylfuran, comprising the following steps: dissolving a hexose into an alcohol to form a hexose solution; contacting the hexose solution with the hydrophobic palladium/MOF (metal organic framework) material as a catalyst and with polymethylhydrosiloxane as a hydrogen donor, and reacting at 70 to 130° C. for 0.25 to 12 h under the action of an acidic additive; and at the end of the reaction, recycling the catalyst via centrifugal separation;
    wherein the concentration of the hexose in the alcohol is 0.2 to 10 wt %;
    wherein the amount of the polymethylhydrosiloxane is 5 to 10 mol % of the amount of the hexose;
    wherein the amount of a hydrophobic palladium/MOF material, based on the amount of Pd, is 0.1 to 5 mol % of the amount of the hexose;
    wherein a MOF is obtained by dissolving a chloride salt or a nitrate salt of $Cu^{2+}$, $Al^{3+}$, $Cr^{3+}$, $Fe^{3+}$, or $Zr^{4+}$, and an equivalent mole number of terepthalic acid in deionized water or N,N-dimethylformamide, performing hydrothermal treatment at 120 to 220° C. for 12 to 72 h, and then performing filtering, washing and vacuum drying;
    wherein the hydrophobic palladium/MOF material is obtained by immersing the MOF serving as a carrier to obtain a palladium/MOF material, reducing the palladium/MOF material in a hydrogen atmosphere at 200 to 300° C. for 2 to 5 h, and finally performing polydimethylsiloxane coating layer processing;
    wherein immersing the MOF comprises dissolving the a Pd salt in water or alcohol, adding the MOF, performing ultrasonic treatment for 15 to 60 min, stirring at room temperature for 12 to 24 h, and then centrifuging, washing, drying and grinding the mixture to obtain the palladium/MOF material;
    wherein the amount of the Pd salt, based on the weight of Pd, is 1 to 20 wt % of the mass of the MOF; the Pd salt is palladium chloride, palladium nitrate, palladium acetate, or palladium sulfate; and the alcohol is methanol, ethanol, n-butanol, or n-hexanol.

9. The process according to claim 8, wherein the hexose is fructose, mannose, glucose, saccharose, cellobiose or inulin; and the alcohol is methanol, ethanol, n-propanol, isopropanol, n-butanol, isobutanol or n-hexanol.

10. The process according to claim 8, wherein the acidic additive is hydrochloric acid, sulfuric acid or chlorobenzene, and the amount of the acidic additive is 3 to 9 mol % of the amount of the hexose.

11. The process according to claim 8, further comprising regenerating the hydrophobic palladium/MOF material by centrifuging out the catalyst material from the reaction liquid, washing the catalyst material with water and ethanol each for 3 to 5 times, performing vacuum drying at 100° C. for 10 h, and grinding the material to obtain a regenerated catalyst material.

12. The process of claim 8, wherein the concentration of hexose in the alcohol is 0.5 to 5 wt %, wherein the amount of the hydrophobic palladium/MOF material, based on the amount of Pd, is 0.5 to 3 mol %, and wherein the amount of the polymethylhydrosiloxane is 6 to 10 mol % of the amount of the hexose.

13. The process of claim 8, wherein immersing the MOF comprises dissolving 1 to 6 wt % Pd salt in water or alcohol, based on the weight of Pd.

14. The process according to claim 8, wherein the concentration of the hexose in the alcohol is 0.5 to 5 wt %;
wherein the amount of the polymethylhydrosiloxane is 6 to 10 mol % of the amount of the hexose;
wherein the amount of the hydrophobic palladium/MOF material, based on the amount of Pd, is 0.5 to 2 mol % of the amount of hexose.

* * * * *